US006277587B1

(12) United States Patent
Lamster

(10) Patent No.: US 6,277,587 B1
(45) Date of Patent: Aug. 21, 2001

(54) METHOD OF TESTING FOR PERIODONTAL DISEASE

(75) Inventor: Ira B. Lamster, Wycoff, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/308,215

(22) PCT Filed: Nov. 12, 1997

(86) PCT No.: PCT/US97/20505

§ 371 Date: May 14, 1999

§ 102(e) Date: May 14, 1999

(87) PCT Pub. No.: WO98/21583

PCT Pub. Date: May 22, 1998

Related U.S. Application Data

(63) Continuation-in-part of application No. 08/746,661, filed on Nov. 14, 1996, now Pat. No. 6,063,588.

(51) Int. Cl.$^7$ .................................................. C12Q 1/34
(52) U.S. Cl. ............................................. 435/18; 435/7.4
(58) Field of Search .......................... 435/7.1, 7.4, 7.92, 435/18, 810; 436/811

(56) References Cited

U.S. PATENT DOCUMENTS

| | | |
|---|---|---|
| 4,966,856 | 10/1990 | Ito et al. . |
| 4,981,787 | 1/1991 | Baram . |
| 5,047,328 | 9/1991 | Chambers et al. . |
| 5,223,403 | 6/1993 | Loesche et al. . |
| 5,272,260 | 12/1993 | Pope et al. . |
| 5,589,328 | 12/1996 | Mahant . |
| 6,063,588 | * 5/2000 | Lamster ................................. 435/18 |

OTHER PUBLICATIONS

Darwish S. Studies on Possible Factors in Saliva in the Etiology of Oral Cancer. Qatar University Science Journal. 14(Special Issue)61–67, 1994.*
Zambon J. Effect of Periodontal Therapy on Salivary Enzymatic Activity. J of Periodontal Research, 20(6)652–659 1985.*
Ding, Y., et al., (1994) "Gingival crevicular fluid and salivary matrix metalloproteinases of heavy smokers as indicators of periodontal health." *Annals of the New York Academy of Science* 732: 453–455 (Exhibit B).
Ferguson, D.B., (1987) "Current diagnostic uses of saliva." *J. Dent. Res.* 66(2): 420–424.
Haffajee, A.D., et al., (1983) "Clinical parameters as predictors of destructive periodontal desease." *J. Clin. Periodontol.* 10: 257–265. (Exhibit C).
Lamster, I.B., et al., (1985) "Evaluation and modification of spectrophotometric procedures for analysis of lactate dehydrogenase, beta–glucuronidase, and arylsulphatase in human gingival crevicular fluid collected with filter–paper strips." *Arch. Oral Biol.* 30: 235–242.

Lamster, I.B., et al., (1988) "Enzyme activity in crevicular fluid for detection and prediction of clinical attachment loss in patients with chronic adult periodontitis: 6 month results." *J. Periodontol.* 59: 516–523.
Lamster, I.B., et al. (1991) "Indicators of the acute inflammatory and humoral immune responses in gingival crevicular fluid: relationship to active periodontal disease".
Lamster, I.B., et al., (1993) "Current status of tests for periodontal disease." *Adv. Dent. Res.* 7(2): 182–190.
Lamster, I.B., et al., (1994) "The relationship of β–glucuronidase activity in crevicular fluid to clinical parameters of periodontal disease: Findings from a multicenter study."
Lamster, I.B. et al., (1994) "Development of a risk profile for periodontal disease: Microbial and host response factors." *J. Periodontol.* 65(5): 511–520.
Lamster, I.B., et al., (1995) "The relationship of β–glucuronidase activity in crevicular fluid to probing attachment loss in patients with adult periodontitis. Findings from a fluid to probing attachment loss in patients with adult periodontitis. Findings from a multicenter study." *J. Clin. Periodontol.* 22: 36–44.
Lamster, I.B., and Grbic J.T. (1995) "Diagnosis of periodontal disease based on analysis of the host response." *Periodontol. 2000* 7: 83–99.
Lundy, F.T. and Lamey, P.J. (1995) "The recovery of proteolytic activity using the salivette® system." *Eur. J. Clin. Chem. Clin. Biochem.* 33: 443–444. (Exhibit D).
Mäkelä, M., et al., (1994) "Matrix metalloproteinases (MMP–2 and MMP–9) of the oral cavity: Cellular origin and relationship to periodontal status." *J. Dent. Res.* 73(8): 1397–1406. (Exhibit E).
Mandel, I.D. (1991) "Marker of periodontal disease susceptibility and activity derived from saliva." In: *Johnson, N.W. ed. Risk markers for oral disease. vol. 3, Periodontal diseases.* London: Cambridge University Press, pp. 228–253.
Mandel, I.D., (1990) "The diagnostic uses of saliva." *J. Oral Pathol. Med.* 19: 119–125.

* cited by examiner

*Primary Examiner*—Ralph Gitomer
(74) *Attorney, Agent, or Firm*—John P. White; Cooper & Dunham LLP

(57) ABSTRACT

This invention provides a method of testing for periodontal disease in a subject which comprises detecting an elevated concentration of β-glucuronidase in saliva from the subject relative to the concentration of β-glucuronidase present in saliva from a healthy subject. The concentration of β-glucuronidase in the subject's saliva is determined by adding to a sample of the saliva a substrate for β-glucuronidase and measuring the amount of a product produced by the action of β-glucuronidase in the substrate. Also, the concentration of β-glucuronidase in the subject's saliva is determined by adding to a sample of saliva a labeled antibody specific for β-glucuronidase and measuring the amount of labeled antibody which forms a complex with β-glucuronidase present in the saliva.

14 Claims, 1 Drawing Sheet

METHOD OF TESTING FOR PERIODONTAL DISEASE

This application is a §371 of PCT International Application No. PCT/US97/20505, filed Nov. 12, 1997, designating the United States of America, which was a continuation-in-part of U.S. Ser. No. 08/746,661 filed Nov. 14, 1996 now U.S. Pat. No. 6,063,588, the content of which is hereby incorporated by reference into the present application.

BACKGROUND OF THE INVENTION

Throughout this application, various publications are referenced by author and date. Full citations for these publications may be found listed alphabetically at the end of the specification immediately before the claims. The disclosures of these publications in their entireties are hereby incorporated by reference into this application in order to more fully describe the state of the art as known to those skilled therein.

Conventional diagnostic evaluation of periodontal disease has relied on measuring clinical parameters, such as probing depth, attachment level, and plaque accumulation, and on measuring the height of the alveolar bone using radiographs. One shortcoming of these conventional tests is that they only define the status of the periodontium at the time of examination. In the past 10 to 15 years, studies have shown that clinical parameters of periodontal disease are poor predictors of when and at which sites patients that would experience active disease (Haffajee, A. D., et al., 1993). In addition, measurement of alveolar bone loss using intraoral radiographs is of limited value because it provides only a historical record of past disease and cannot be used to determine when the loss of crestal bone occurred.

Due to these limitations, researchers have investigated alternative methods for evaluating patients with periodontal disease (Lamster, I. B., et al., 1993).

Previously, analysis of the host inflammatory and immune responses in periodontal disease has been performed on gingival crevicular fluid (GCF). Among the host-derived mediators shown to identify patients at risk for active periodontal disease is the lysosomal enzyme, β-glucuronidase (Lamster, I. B., et al., 1988; Lamster, I. B., et al., 1995), which is a marker of primary granule release from neutrophils into the gingival crevicular fluid. Lamster and coworkers previously found that elevated levels of β-glucuronidase in gingival crevicular fluid were diagnostic for existing periodontal disease, and correlated with the likelihood of future disease progression (Lamster, I. B., et al., 1994; Lamster, I. B., et al., 1995). Existing tests for β-glucuronidase in gingival crevicular fluid involve collecting fluid from within the gingival crevice using such special devices as methylcellulose strips or microsyringes. The levels of β-glucuronidase are measured in the fluid by adding a substrate for β-glucuronidase which in the presence of the enzyme produces a product that is detectable. Unfortunately, this method is labor-intensive and requires the services of highly-trained personnel, such as a dentist or dental hygienist. Therefore, although measurements of β-glucuronidase levels in gingival crevicular fluid have been shown to be a better indicator of human periodontal disease than previous conventional evaluations, the limitations of this method make its widespread use unlikely. Currently no method exists that overcomes these disadvantages and provides a simple, reliable test for diagnosing periodontal disease which could be utilized on a widespread basis.

Although one might consider using samples from other body fluids such as saliva that are easy to collect, distinct drawbacks for biochemical evaluation of periodontal disease by analysis of saliva exist (Lamster, I. B. and Grbic, J. T., 1995).

More specfiically, based on the current state of the art as described in the scientific literature, it would have been expected to be difficult, if possible, to detect elevated levels of β-glucuronidase in saliva as a means of diagnosing periodontal disease (Ding, Y., et al., 1994; Lundy, F. T. and Lamey, P-J., 1995). Thus, detection of markers in general is more difficult in saliva than in gingival crevicular fluid because constituents of saliva are derived from many sources, including the major and minor salivary glands and from gingival crevicular fluid. (Lamster, I. B. and Grbic, J. T., 1995). Further, the relatively large volumes of fluid involved when dealing with saliva would be expected to have both a masking and a diluting effect on any potentially important marker derived from gingival crevicular fluid (Lamster, I. B. and Grbic, J. T., 1995), thus making it difficult to detect the marker.

Moreover, even if detection of the enzyme in saliva was possible, one would have expected that it would be difficult to distinguish between healthy and diseased subjects. Although previous studies have proposed diagnostic tests in saliva for periodontal disease using markers such as IgG, IgA and collagenase, none has ever mentioned the use of β-glucuronidase. (Lamster, I. B. and Grbic, J. T., 1995). In fact, some experts have argued that elevated levels of markers in saliva would not be detectable until after disease had become widespread, thereby limiting the importance of such an approach for diagnositic purposes (Mandel, I., 1991). Furthermore, even if β-glucuronidase was detectable, one could reasonably have expected that the dilution of the marker by the much larger volume of saliva would have made it impossible to distinguish between healthy and diseased subjects.

Based on the foregoing, one skilled in the art would not have expected that a test for measuring the concentration of β-glucuronidase in saliva would be useful for the diagnosis of periodontal disease. Unexpectedly, a saliva test based on measuring levels of β-glucuronidase has not only proven useful, it has proven to be a better discriminator of periodontitis than analysis of gingival crevicular fluid or clinical parameters.

SUMMARY OF THE INVENTION

This invention provides a method of testing for periodontal disease in a subject which comprises detecting an elevated concentration of β-glucuronidase in saliva from the subject relative to the concentration of β-glucuronidase present in saliva from a healthy subject.

This invention further provides that the concentration of β-glucuronidase in the subject's saliva may be determined by adding to a sample of saliva or a sample derived from saliva a substrate for β-glucuronidase and measuring the concentration of a product produced by the action of β-glucuronidase in the substrate.

In one embodiment of this invention, the product produced by the action of β-glucuronidase on the substrate is characterized by the property of being fluorescent, visible or detectable by spectrophotometry. Examples of suitable substrates include 4-methylumbelliferone β-D glucuronide or phenolphthalein mono-β-glucuronic acid.

This invention further provides a method of testing for periodontal disease, wherein the concentration of β-glucuronidase in the subject's saliva is determined by adding to a sample of saliva a labeled antibody specific for β-glucuronidase and measuring the amount of labeled antibody which forms a complex with β-glucuronidase present in the saliva.

This invention further provides a test kit for performing the above-described method.

DETAILED DESCRIPTION OF THE INVENTION

Figure 1:
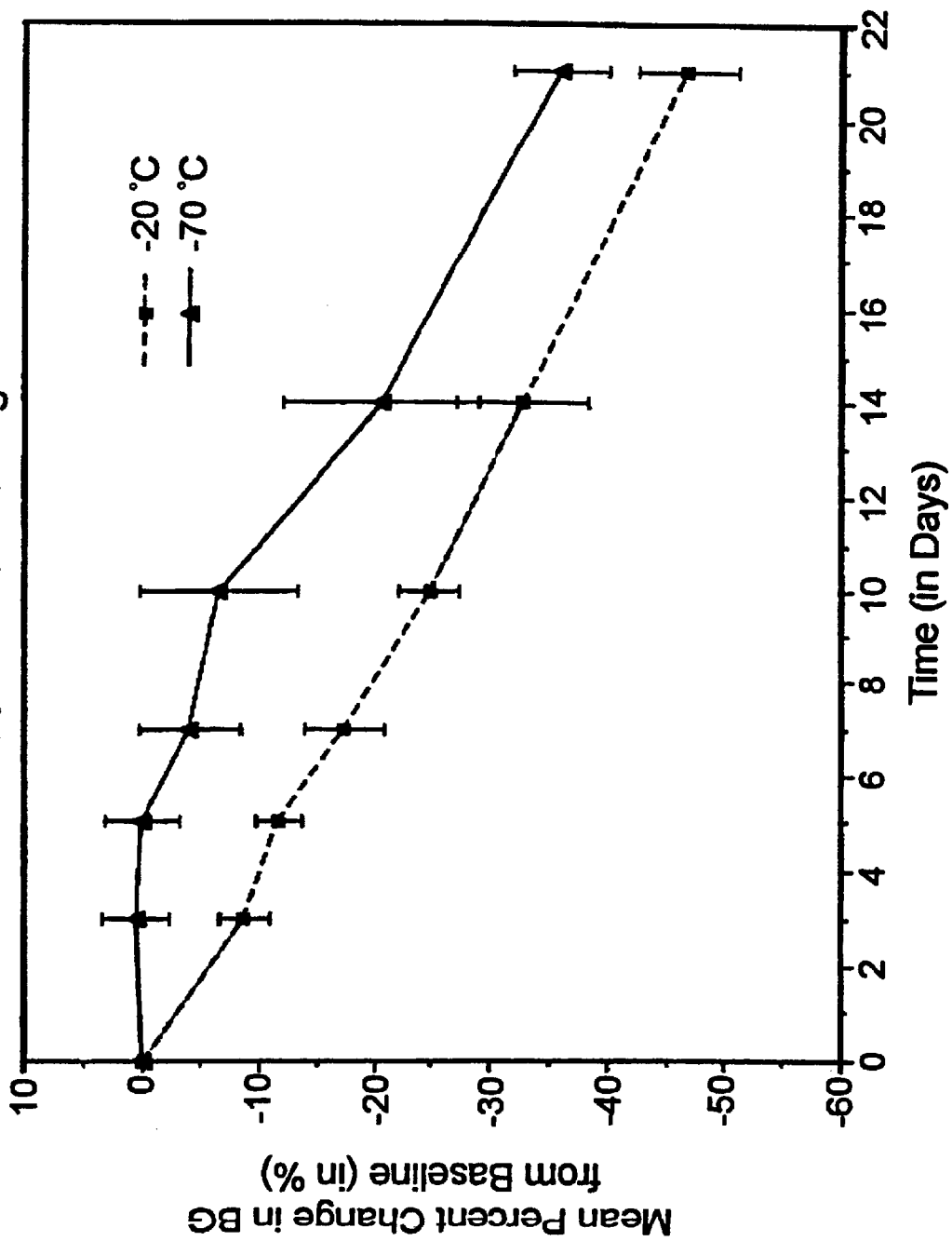
FIG. 1. Retention of β-glucuronidase activity in saliva samples with freezing. Saliva samples from patients with varying degrees of periodontal disease were aliquoted and frozen at either −20° C. or −70° C., and the concentration of β-glucuronidase was determined at day 0 (date of collection, unfrozen), 3, 5, 7, 10, 14 and 21. The concentration of β-glucuronidase in samples frozen at either −20° C. or −70° C. were compared to the concentration of β-glucuronidase in a room-temperature sample taken at day 0. Data are reported as mean percent change (loss) of activity at each time interval.

The present invention provides a method of testing for periodontal disease in a subject which comprises detecting an elevated concentration of β-glucuronidase in saliva from the subject relative to the concentration of β-glucuronidase present in saliva from a healthy subject.

As used in this application, "periodontal disease" means periodontitis which is characterized by the presence of increased probing depth (one or more sites with a depth of at least 5 mm), evidence of clinical attachment loss and demonstrable loss of alveolar bone on periapical and bitewing dental radiographs. Periodontal disease occurs as a consequence of the host's inflammatory and immune responses to subgingival bacterial pathogens. The symptoms include erythematous (red) and edematous (swollen) gingiva, pocket formation around the teeth, tooth mobility and eventually tooth loss.

As used in this application, "an elevated concentration of β-glucuronidase" means that the concentration of β-glucuronidase in saliva from the subject is larger than the concentration of β-glucuronidase in saliva from a subject who is not afflicted with periodontal disease. A saliva sample from a subject who is not afflicted with periodontal disease should have minimal or negligible amounts of β-glucuronidase. These levels of β-glucuronidase will be lower in comparison to the levels of this enzyme in saliva from periodontitis patients.

Further, as used in this application, "a healthy subject" is defined as one who is not afflicted with human periodontal disease.

This invention also provides a method of testing for periodontal disease in a subject by detecting an elevated concentration of β-glucuronidase, wherein the concentration of β-glucuronidase in the subject's saliva is determined by adding to a sample of the saliva a substrate for β-glucuronidase and measuring the amount of a product produced by the action of β-glucuronidase in the substrate.

In a preferred embodiment, the sample of saliva is unstimulated. As used in this application, "unstimulated" saliva means that the subject will expectorate in a collection vessel without stimulation of salivary flow, for example, by having the subject chew on a piece of paraffin film or a tart candy.

As used in this application, a "substrate" means any molecule upon which the enzyme β-glucuronidase acts to produce a product that is neither β-glucuronidase nor the substrate. Substrates for the enzyme β-glucuronidase are well-known in the art, and include 4-methylumbelliferone β-D glucuronide which yields the product 4-methylumbelliferone, and phenolphthalein mono-β-glucuronic acid which yields the product phenolphthalein.

Methods of measuring the concentration of product produced by the action of β-glucuronidase are also well-known in the art. In one preferred embodiment of the invention, the amount of the product is measured based upon the product being characterized by the property of being fluorescent.

In another embodiment of the invention, the amount of the product is measured based upon the product being detectable by colorimetry. Due to negligible levels of β-glucuronidase in healthy individuals, the elevated concentrations of β-glucuronidase in periodontitis patients will act upon certain substrates so that one can either visualize and measure by colorimetric devices the concentration of β-glucuronidase in a saliva sample.

In another embodiment of the invention, the amount of the product is measured based upon the product being detected by spectrophotometry. For example, when β-glucuronidase acts upon phenolphthalein mono-β-glucuronic acid in an alkaline solution, the product produced is phenolphthalein, the concentration of which may be measured using a spectrophotometer.

This invention further provides a method of testing for periodontal disease in a subject by detecting an elevated concentration of β-glucuronidase by adding to a sample of saliva a labeled antibody specific for β-glucuronidase and measuring the amount of labeled antibody which forms a complex with β-glucuronidase present in the saliva.

The labeled antibody may be a polyclonal or monoclonal antibody. In one embodiment, the labeled antibody is a purified, labeled antibody. In another embodiment, the labeled antibody may consist of two antibodies. For instance, a first antibody may specifically bind to β-glucuronidase and not be labeled. A second antibody is directed against the first antibody and is labeled with a detectable marker or an enzyme which gives rise to a detectable marker.

The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, radioactive or fluorescent.

In another embodiment of this invention, the concentration of β-glucuronidase in the subject's saliva may be determined based upon measuring the concentration of β-glucuronidase in a sample derived from saliva.

As used in this application, "derived from saliva" means a sample initially collected as whole saliva, but due to manipulation of the sample, only specific components remain in the sample. Methods of manipulating samples in such manner are well-known in the field. In one such embodiment, the sample derived from the saliva is supernatant saliva. As used herein, "supernatant saliva" is saliva that has had the cellular components removed. Methods of removing cellular components from saliva are well known in art, and include filtration, ion exchange chromatography and precipitation. In one such embodiment, the whole saliva is centrifuged and the supernatant is collected.

In an embodiment of the above-described method, the sample saliva or the sample derived from saliva is mixed and incubated with the appropriate substrate at room temperature (20–24° C.). In another embodiment, the mixing and incubation step occur over a period of about fifteen minutes.

In another embodiment, the sample derived from the saliva may be frozen before the concentration of β-glucuronidase is measured. Further, the concentration of β-glucuronidase may be measured days after the sample is collected and frozen. In a specific embodiment, the concentration of β-glucuronidase is detected about 5 days after the saliva is frozen at −70° C.

This invention is illustrated in the Experimental Details section which follows. This section is set forth to aid in an understanding of the invention but is not intended to, and should not be construed to, limit in any way the invention as set forth in the claims which follow thereafter.

1. Experimental Details

EXAMPLE 1

A. Methods and Materials (1) Study Subjects

A total of 12 individuals were evaluated in this pilot study. Six were classified as periodontally healthy, and 6 were classified as presenting with existing periodontitis. All were at least 16 years of age. All participants were medically healthy, and did not present any other medical diagnosis (i.e. diabetes mellitus) that could effect their periodontal status. None of the participants were using medications that could effect the periodontal tissues (i.e. NSAIDS or antibiotics), and none required antibiotic prophylaxis prior to a dental appointment. All had a minimum of 20 natural teeth, with a minimum of 10 posterior teeth.

The healthy subjects were required to have a mean probing depth of ~2.5 mm, while the patients with periodontitis were studied if their mean probing depth was >3.0 mm. The mean age of the healthy controls was 25.2 years and there were 4 females and 2 males. For the patients with periodontitis the mean age was 38.8 years, and there was 5 females and 1 male. The healthy controls had an average of 26.8 teeth, while the periodontitis patients had an average of 25.2 teeth.

(2) Clinical Protocol

A standard clinical protocol was followed.
1. 5 ml of unstimulated whole saliva was collected in a plastic test tube (marked "#1").
2. Gingival crevicular fluid was collected from the mesiobuccal sites of all teeth, except the third molars, by the technique described by Lamster, et al. (Lamster, I. B., et al., 1994; Lamster, I. B., et al., 1995).
3. Clinical data was collected from all sites, including measurements of probing depth (mm), recession (mm), bleeding on probing (yes or no, 20 seconds after probing) and the presence of supragingival plaque (yes or no).
4. Immediately after the completion of the clinical examination, 5 ml of unstimulated whole saliva was collected in a plastic test tube (marked "#2").
5. The study participant rinsed for 30 seconds with a small cup of water, and then expectorated.
6. 5 ml of unstimulated whole saliva was then immediately collected into a plastic test tube (marked "#3").
7. 5 minutes later, 5 ml of unstimulated whole saliva was collected into a plastic test tube (marked "#4").
8. 5 minutes after collection of "#4", 5 ml of unstimulated whole saliva was collected in a plastic test tube (marked "#5").

All clinical data and saliva samples were collected by a single periodontist, and the estimated patient contact time was a total of 30 minutes for the examination and collection of all samples.

(3) Analysis of β-glucuronidase in Gingival Crevicular Fluid and Saliva

The gingival crevicular fluid samples were prepared for analysis as previously described (Lamster, I. B., et al., 1995; Lamster, I. B., et al., 1994). After collection of salivary samples, the whole unstimulated saliva was analyzed for β-glucuronidase by resuspension and removal of 50 μl. The residual fluid from the sample was centrifuged at 6500 RPM for 10 minutes and 50 μl of supernatant was removed from the test tube and analyzed for β-glucuronidase.

The basic assay procedure involves 5 steps:

1. add 50 μl of control, standard or sample
2. add 100 μl of substrate
3. mix and incubate at room temperature for 15 minutes
4. add 2 ml of glycine buffer, pH 11.7
5. mix and measure fluorescence The specific biochemical procedure for analysis of β-glucuronidase in biologic samples is described below.

Into properly designated tubes, add 50 μl (in duplicate) of saline control, standards and samples, as follows:

For saline controls, 0.9% saline. For enzyme standards, 1 International Unit (I.U.) and 2 I.U., respectively, of stock β-glucuronidase. For substrate standards, 0.008 mM and 0.016 mM, respectively, of 4-methylumbelliferone. For each tube, add 100 μl of substrate solution (3.7 mM. methylumbelliferone β-D glucuronide, containing 0.001% BSA). Mix and incubate at room temperature (20–24° C.) for 15 minutes. The reaction is halted with 2 ml of 0.2 M glycine buffer, pH 11.7, containing 0.2% sodium diodecyl sulfate. Mix and within 60 minutes after halting the reaction, measure fluorescence in a fluorometer (Fluor-Tec, St. Johns Associates) with a primary wavelength of 360 nm, and secondary wavelength of 450 nm, setting 1 I.U. of β-glucuronidase at 100 units. Two (2) I.U. of β-glucuronidase should read between 180 units and 220 units, and 0.008 mM and 0.016 mM of 4-methylumbelliferone should read approximately 100 units and 200 units, respectively.

B. Results

Where appropriate, mean values for all clinical variables, and gingival crevicular fluid and saliva levels of β-glucuronidase were calculated for each patient, and then group means were determined (healthy subjects, patients with periodontitis). The difference between groups was determined by ANOVA. In addition, the relative risk was calculated, using the healthy subjects as the unaffected control group.

(1) Clinical Parameters (Table 1)

The mean probing depth±standard error for the controls was 2.47±0.08 mm, while for the periodontal patients this value was 3.41±0.09 mm (p<0.0001). The relative risk for increased probing depth associated with periodontitis was 1.38. A similar pattern was seen for attachment level. The percent of sites displaying bleeding on probing was significantly higher for the periodontitis patients (31.6±22.4%) compared to the control subjects (5.6±6.5%; p.<0.02). For bleeding on probing the relative risk was 5.68, which was the highest risk observed for the clinical parameters. The percent of sites with plaque was not significantly different between groups.

TABLE 1

Comparison between the healthy and periodontitis groups for mean clinical parameters.

| Clinical parameters | Healthy subjects | Periodontitis patients | p | RR[1] |
|---|---|---|---|---|
| Probing depth (mm) | 2.47 ± 0.08 | 3.41 ± 0.09 | >.0001 | 1.38 |
| Attachment level (mm) | 2.47 ± 0.08 | 3.68 ± 0.18 | .0001 | 1.49 |
| Bleeding on probing (%) | 5.6 ± 2.7 | 31.6 ± 9.1 | .0208 | 5.68 |
| Plaque (%) | 31.5 ± 8.0 | 41.0 ± 6.2 | .3752 | 1.3 |

[1]RR = relative risk, periodontitis patients/healthy patients (2) β-glucuronidase in Gingival Crevicular Fluid (Table 2)

The mean amount of β-glucuronidase in gingival crevicular fluid was significantly greater for the periodontitis patients (59.8±14.9 units) compared to the control subjects (16.8±5.8 units; p.<0.0001). The relative risk was 3.57.

(3) β-glucuronidase in Saliva (Table 2)

(a) Whole Saliva

There were 5 saliva samples, and in general the differences between diseased patients and healthy controls was greater than what was observed for the clinical or gingival crevicular fluid parameters. At the initiation of the study, the mean β-glucuronidase in whole saliva for the patients was 132.8±22.9 units versus 24.7±18.5 units for the controls (p=0.0012). The relative risk was 5.39. The relative risk for the second through fifth samples were 4.26, 4.25, 5.67 and 7.59, respectively. Differences between groups in terms of actual β-glucuronidase units were significant in all but the second set of samples; however, statistical significance was approached (p=0.068).

(b) Supernatant Saliva

Following centrifugation, analysis of β-glucuronidase in the salivary supernatants revealed larger differences between diseased and healthy subjects compared to clinical, gingival crevicular fluid or whole saliva samples. From the first through the fifth samples, the relative risk was 9.26, 9.17, 13.61, 7.95 and 8.42., respectively. Differences between healthy and diseased groups, in terms of actual β-glucuronidase units, was significant only in the first and second sets of samples, however. This is due to the large variance in β-glucuronidase activity observed between periodontitis samples.

TABLE 2

Comparison between the healthy and periodontitis groups for gingival crevicular fluid and salivary levels of β-glucuronidase. All values in units.

| Sample | | Healthy subjects | Periodontitis patients | p | RR[1] |
|---|---|---|---|---|---|
| a. GCF | | 16.8 ± 2.4 | 59.8 ± 6.1 | <.0001 | 3.57 |
| b. Whole saliva | #1 | 24.7 ± 7.5 | 132.8 ± 22.9 | .0012 | 5.39 |
| | #2 | 28.1 ± 2.7 | 119.6 ± 44.6 | .0678 | 4.26 |
| | #3 | 13.0 ± 1.6 | 55.3 ± 17.0 | .0324 | 4.25 |
| | #4 | 10.6 ± 1.5 | 60.3 ± 17.8 | .0195 | 5.67 |
| | #5 | 8.1 ± 1.8 | 61.2 ± 17.8 | .0141 | 7.59 |
| c. Supernatant saliva | #1 | 7.1 ± 1.5 | 65.6 ± 17.9 | .0088 | 9.26 |
| | #2 | 6.9 ± 1.2 | 63.0 ± 18.7 | .0135 | 9.17 |
| | #3 | 3.0 ± 1.3 | 40.4 ± 20.4 | .0967 | 13.61 |
| | #4 | 4.8 ± 1.2 | 38.4 ± 20.1 | .1257 | 7.95 |
| | #5 | 4.4 ± 0.6 | 36.8 ± 19.5 | .1281 | 8.42 |

[1]RR = relative risk, periodontitis patients/healthy patients

C. Discussion

A number of reviews have examined the diagnostic significance of salivary analysis (Ferguson, D. B., 1987; Mandel, I. D., 1990). In general, the analysis of saliva for diagnostic purposes has been directed towards evaluating systemic disease (i.e. Sjögren's syndrome, cystic fibrosis, HIV infection) or as a means of determining systemic levels of therapeutic drugs (i.e. steroids).

The results of this pilot study suggest that evaluation of β-glucuronidase in unstimulated whole saliva or the salivary supernatant can discriminate between patients with adult periodontitis and healthy controls. The degree of discrimination between healthy and diseased patients as measured by the relative risk is better with assessment of β-glucuronidase in saliva than with clinical parameters or gingival crevicular fluid analysis. Sample collection and analysis is accomplished quickly compared to conventional methods using clinical parameters or gingival crevicular fluid. Further, sample collection requires only a minimally trained office personnel. The application of such a test will be valuable in the identification/screening of patients with periodontitis.

Analysis of β-glucuronidase in saliva can, for example, be employed to screen patients for periodontitis in a general dentist's office. As currently designed, applicants' fluorometric assay provides a quantitative value of the level of β-glucuronidase in saliva, and can be performed during the time the patient is in the office, thereby allowing the findings to be communicated to the patient before the conclusion of their office visit. Further, this test can be modified to a colormetric assay that would provide a semiquantitative or qualitative reading. This type of assay can be used in a home test format that would signal the need for the patient to be evaluated by a dentist for periodontal disease.

As described in this application, detecting the concentration of β-glucuronidase in a subject's saliva is an easy, reliable method of testing for the subject's existing periodontal disease. Previously, testing the levels of β-glucuronidase in gingival crevicular fluid proved effective for predicting the risk for development of active periodontal disease because elevated levels of the enzyme were associated with an increased risk. Since β-glucuronidase in saliva originates from β-glucuronidase in gingival crevicular fluid, one could believe that detection of β-glucuronidase levels in saliva would prove also effective for prognostic purposes.

EXAMPLE 2

In a specific embodiment of the above-described invention, applicants further tested the efficacy of the invention on frozen samples.

A. Methods and Materials (1) Study Subjects

All participants were medically healthy, i.e. no medications or diseases that would affect their periodontal status. Any patient requiring antibiotic prophylaxis was not eligible. Further, the following criteria were considered in order to enter this study:

a. No history of periodontal treatment within the last year;

b. Minimum of 20 teeth in dentition with 10 being posterior teeth; and c. At least 18 years or older.

A total of 9 individuals with varying degrees of periodontal disease were evaluated in this study.

(2) Clinical Protocol

The standard clinical protocol was as follows:

A 5 to 10 ml sample of unstimulated saliva was collected from each patient. The saliva sample were first divided into 50 μl aliquots. One sample was analyzed in duplicate for β-glucuronidase concentration on day 0 (date of collection, not frozen). Using the method described above, the remaining sets of samples were analyzed for β-glucuronidase concentration at the following time points: day 3, day 5, day 7, day 10, day 14 and day 21. For each day, the samples were in duplicate and frozen at either −20° C. or −70° C. (FIG. 1).

B. Results

Based on the β-glucuronidase concentrations detected in the samples frozen at either −20° C. or −70° C., applicants charted the mean percent change in concentration from these samples as compared to the concentration in a unfrozen sample collected at day 0 (FIG. 1).

As indicated in FIG. 1, the β-glucuronidase activity of samples frozen at −70° C. were comparable to the baseline activity until about day 5. The retention of β-glucuronidase activity by samples frozen at −70° C. for at least 5 days after collection shows one could reliably use the aforementioned method of detecting periodontal disease in patients some days after collection of the samples by freezing the samples.

As further indicated in FIG. 1, the activity of β-glucuronidase in samples frozen at either −20° C. or −70° C. declined steadily and constantly up until the last day of data collection, day 21. After plotting the retention of β-glucuronidase activity, applicants observed the constant decline in activity was consistently related to the passage of time, regardless of the temperature at which the samples were frozen. Therefore, depending on the day in which the aforementioned test is performed, one could extrapolate the concentration of β-glucuronidase detected in the sample to determine the original concentration of β-glucuronidase in the patients' sample on the day of collection.

D. Conclusion

Using the aforementioned method of detecting elevated levels of β-glucuronidase in saliva is an easy, reliable method of testing for the subject's existing periodontal disease status. Previous methods of testing in β-glucuronidase in gingival crevicular fluid proved effective for predicting the risk for development of active periodontal disease. Therefore, since β-glucuronidase in saliva originates from β-glucuronidase in gingival crevicular fluid, detection of β-glucuronidase levels in saliva will prove effective and definitely less arduous.

Furthermore, as a specific embodiment of the invention, applicants have shown that one can freeze saliva samples, and still reliably determine the concentration of β-glucuronidase using the aforementioned method of detection.

Still further, one can also reliably detect concentrations of β-glucuronidase using frozen samples that have been laid aside for testing at a later time. As determined in applicant's experiments, the results from samples frozen at either −20° C. or −70° C. show that the aforementioned test is effective and reliable. Lastly, the linear rate of loss of β-glucuronidase activity in saliva with freezing provides evidence that the assay is both reliable and reproducible.

These embodiments of the invention will prove invaluable due to the added convenience to the technician and clinician. One need not immediately test samples to accurately determine the concentration levels of β-glucuronidase in the sample. One could freeze these samples and store them away until a more convenient time, thereby saving time, and eventually expense.

REFERENCES

1. Ding, Y., et al., (1994) "Gingival crevicular fluid and salivary matrix metalloproteinases of heavy smokers as indicators of periodontal health." *Annals of the New York Academy of Science* 732: 453–455
2. Ferguson, D. B., (1987) "Current diagnostic uses of saliva." *J Dent Res* 66(2):420–424.
3. Haffajee, A. D., et al., (1993) "Clinical parameters as predictors of destructive periodontal disease." *J Clin Periodontol* 10:257–265.
4. Lamster, I. B., et al., (1985) "Evaluation and modification of spectrophotometric procedures for analysis of lactate dehydrogenase, beta-glucuronidase, and arylsulphatase in human gingival crevicular fluid collected with filter-paper strips." *Arch. Oral Biol.* 30: 235–242.
5. Lamster, I. B., et al., (1988) "Enzyme activity in crevicular fluid for detection and prediction of clinical attachment loss in patients with chronic adult periodontitis: 6 month results." *J Periodontol* 59:516–523.
6. Lamster, I. B., et al., (1993) "Current status of tests for periodontal disease." *Adv Dent Res* 7(2):182–190.
7. Lamster, I. B., et al., (1994) "The relationship of b-glucuronidase activity in crevicular fluid to clinical parameters of periodontal disease: Findings from a multicenter study." *J Clin Periodontol* 21:118–127.
8. Lamster, I. B., et al., (1995) "The relationship of b-glucuronidase activity in crevicular fluid to probing attachment loss in patients with adult periodontitis. Findings from a multicenter study." *J Clin Periodontol* 22:36–44.
9. Lamster, I. B., and Grbic J T (1995) "Diagnosis of periodontal disease based on analysis of the host response." *Periodontol* 2000 7:83–99.
10. Lundy, F. T and Lamey, P.-J. (1995) "The recovery of proteolytic activity using the salivette® system." *Eur. J. Clin. Chem. Clin. Biochem.* 33: 443–444.
11. Mäkelä, M., et al., (1994) "Matrix metalloproteinases (MMP-2 and MMP-9) of the oral cavity: Cellular origin and relationship to periodontal status." *J Dent Res* 73(8): 1397–1406.
12. Mandel, I. D. (1991) "Marker of periodontal disease susceptibility and activity derived from saliva." In: Johnson. N. W. ed. Risk markers for oral disease. Vol. 3. *Periodontal diseases*. London: Cambridge University Press, pp. 228–253.
13. Mandel, I. D., (1990) "The diagnostic uses of saliva." *J Oral Pathol Med* 19:119–125.

What is claimed is:

1. A method of diagnosing periodontal disease in a subject which comprises:
   (a) collecting saliva from the subject;
   (b) freezing the saliva collected in step (a) for a period of time during which β-glucuronidase activity is retained;
   (c) thawing the frozen saliva of step (b);
   (d) determining a concentration of β-glucuronidase in the saliva from step (c) and
   (e) comparing the concentration of β-glucuronidase determined in step (d) to a concentration of β-glucuronidase in saliva from individuals without periodontal disease, wherein a larger concentration of β-glucuronidase in saliva in step (d) than in saliva from individuals without periodontal disease indicates a diagnosis of periodontal disease in the subject.

2. The method of claim 1, wherein the concentration of β-glucuronidase in the subject's saliva is determined by adding to a sample of the saliva a substrate for β-glucuronidase and measuring the concentration of a product produced by the action of β-glucuronidase on the substrate.

3. The method of claim 2, wherein the concentration of the product is measured by the fluorescence of the product.

4. The method of claim 2, wherein the substrate is phenolphthalein mono-β-glucuronic acid and the product is phenolphthalein.

5. The method of claim 4, wherein the concentration of the product is measured by a colorimetric device.

6. The method of claim 2, wherein the concentration of the product is measured by a colorimetric device.

7. The method of claim 4, wherein the concentration of the product is measured by a spectrometer or fluorometer.

8. The method of claim 2, wherein the concentration of the product is measured by a spectrometer or fluorometer.

9. The method of claim 1, wherein the concentration of β-glucuronidase is determined about 5 days after the saliva is frozen at −70° C. or −20° C.

10. The method of claim 1, wherein the substrate is 4-methylumbelliferone β-D glucuronide and the product is 4-methylumbelliferone.

11. The method of claim 10, wherein the concentration of the product is measured by the fluorescence of the product.

12. The method of claim 1, wherein the concentration of β-glucuronidase in the subject's saliva is determined by adding to a sample of saliva a labeled antibody specific for β-glucuronidase and measuring the amount of labeled antibody which forms a complex with β-glucuronidase present in the saliva.

13. The method of claim 1, wherein the concentration of β-glucuronidase in the subject's saliva is determined based upon measuring the concentration of β-glucuronidase in a sample derived from the saliva.

14. The method of claim 13, wherein the saliva is supernatant saliva.

* * * * *